United States Patent
Kapadia

(10) Patent No.: US 10,213,304 B2
(45) Date of Patent: Feb. 26, 2019

(54) APPARATUS, SYSTEM, AND METHOD FOR TREATING A REGURGITANT HEART VALVE

(71) Applicant: THE CLEVELAND CLINIC FOUNDATION, Cleveland, OH (US)

(72) Inventor: Samir Kapadia, Chagrin Falls, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 531 days.

(21) Appl. No.: 14/883,819

(22) Filed: Oct. 15, 2015

(65) Prior Publication Data

US 2016/0030166 A1 Feb. 4, 2016

Related U.S. Application Data

(62) Division of application No. 13/559,900, filed on Jul. 27, 2012, now Pat. No. 9,161,837.

(Continued)

(51) Int. Cl.
*A61F 2/24* (2006.01)
*A61M 29/02* (2006.01)

(52) U.S. Cl.
CPC ............ *A61F 2/246* (2013.01); *A61F 2/2466* (2013.01); *A61M 29/02* (2013.01); *A61F 2250/001* (2013.01); *A61F 2250/0004* (2013.01)

(58) Field of Classification Search
CPC ................... A61F 2/2466; A61F 2/246; A61F 2250/0004; A61F 2002/9517; A61M 29/02; A61B 2017/00243

(Continued)

(56) References Cited

U.S. PATENT DOCUMENTS 6,152,144 A    11/2000  Lesh et al.
7,282,023 B2 * 10/2007  Frering .................. A61F 2/004
                                              600/31

(Continued)

FOREIGN PATENT DOCUMENTS

WO    2008141322 A1    11/2008
WO    2009053952 A2    4/2009

OTHER PUBLICATIONS

PCT International Search Report and Written Opinion for PCT/US2012/048499, dated Jan. 23, 2013, pp. 1-12.

*Primary Examiner* — David C Eastwood
(74) *Attorney, Agent, or Firm* — Tarolli, Sundheim, Covell & Tummino LLP

(57) ABSTRACT

An apparatus for treating regurgitation of blood through a diseased heart valve having at least two leaflets includes a lollipop-shaped body member having a proximal end portion, a distal end portion, and an intermediate portion extending between the end portions. The intermediate portion includes an expandable occluding member having an adjustable diameter so that, during at least a portion of the cardiac cycle, at least one of the heart leaflet coapts with a portion of the occluding member to mitigate or prevent regurgitation of blood through the diseased heart valve. The proximal end portion is physically connected to the occluding member and includes a connecting mechanism for operably mating with an adjustment member for adjusting the position and diameter of the occluding member within the diseased heart valve. The distal end portion includes an anchoring member for securing the apparatus in a heart chamber containing the diseased heart valve.

8 Claims, 17 Drawing Sheets

Related U.S. Application Data

(60) Provisional application No. 61/512,170, filed on Jul. 27, 2011.

(58) Field of Classification Search
USPC ..... 600/16, 37; 606/191–200; 623/2.1, 2.11, 623/2.2, 2.36, 2.38
See application file for complete search history.

(56) References Cited

U.S. PATENT DOCUMENTS

| | | | |
|---|---|---|---|
| 8,092,525 B2 | 1/2012 | Eliasen et al. | |
| 8,216,302 B2 | 7/2012 | Wilson | |
| 8,449,606 B2 | 5/2013 | Eliasen et al. | |
| 8,480,730 B2 | 7/2013 | Maurer et al. | |
| 8,486,136 B2 | 7/2013 | Maurer et al. | |
| 8,506,623 B2 | 8/2013 | Wilson et al. | |
| 8,517,915 B2 * | 8/2013 | Perron | A61F 5/0056 600/37 |
| 8,523,883 B2 | 9/2013 | Saadat | |
| 8,597,347 B2 | 12/2013 | Maurer et al. | |
| 8,778,017 B2 | 7/2014 | Eliasen et al. | |
| 8,784,480 B2 | 7/2014 | Taylor et al. | |
| 2002/0042628 A1 | 4/2002 | Chin et al. | |
| 2004/0143283 A1 * | 7/2004 | McGill | A61M 25/0136 606/192 |
| 2004/0204738 A1 | 10/2004 | Weber et al. | |
| 2004/0243227 A1 | 12/2004 | Vidlund et al. | |
| 2005/0015109 A1 | 1/2005 | Lichtenstein | |
| 2005/0149182 A1 | 7/2005 | Alferness et al. | |
| 2005/0222488 A1 | 10/2005 | Chang et al. | |
| 2006/0241745 A1 | 10/2006 | Solem | |
| 2006/0276890 A1 | 12/2006 | Solem et al. | |
| 2007/0061010 A1 | 3/2007 | Hauser et al. | |
| 2007/0066863 A1 | 3/2007 | Rafiee et al. | |
| 2007/0093890 A1 | 4/2007 | Eliasen et al. | |
| 2007/0213751 A1 * | 9/2007 | Scirica | A61F 5/0053 606/157 |
| 2007/0255399 A1 * | 11/2007 | Eliasen | A61F 2/246 623/2.36 |
| 2007/0265700 A1 | 11/2007 | Eliasen et al. | |
| 2007/0293943 A1 * | 12/2007 | Quinn | A61F 2/246 623/2.11 |
| 2008/0086164 A1 | 4/2008 | Rowe | |
| 2008/0109069 A1 | 5/2008 | Coleman et al. | |
| 2008/0119889 A1 | 5/2008 | Kusleika | |
| 2008/0125861 A1 | 5/2008 | Webler et al. | |
| 2008/0147180 A1 | 6/2008 | Ghione et al. | |
| 2008/0288061 A1 | 11/2008 | Maurer et al. | |
| 2009/0030510 A1 | 1/2009 | Ho | |
| 2009/0131849 A1 | 5/2009 | Maurer et al. | |
| 2009/0240326 A1 * | 9/2009 | Wilson | A61F 2/246 623/2.11 |
| 2010/0161043 A1 | 6/2010 | Maisano et al. | |
| 2010/0298929 A1 | 11/2010 | Thornton et al. | |
| 2010/0324668 A1 | 12/2010 | Maurer et al. | |
| 2011/0077733 A1 | 3/2011 | Solem et al. | |
| 2011/0124950 A1 | 5/2011 | Foster | |
| 2011/0282127 A1 | 11/2011 | Cui | |
| 2012/0209377 A1 | 8/2012 | MacHold et al. | |
| 2013/0041459 A1 | 2/2013 | Wilson et al. | |
| 2013/0053882 A1 | 2/2013 | Hocking et al. | |

\* cited by examiner

APPARATUS, SYSTEM, AND METHOD FOR TREATING A REGURGITANT HEART VALVE

RELATED APPLICATION

This application is a divisional application of U.S. patent application Ser. No. 13/559,900, filed Jul. 27, 2012, which claims the benefit of U.S. Provisional Patent Application Ser. No. 61/512,170, filed Jul. 27, 2011. The subject matter of each of the aforementioned applications is hereby incorporated by reference for all purposes.

TECHNICAL FIELD

The present invention relates to an apparatus and method for treating and improving the function of dysfunctional heart valves. More particularly, the present invention relates to a selectively adjustable apparatus that passively assists in closing the native heart valve leaflets to improve valve function of a regurgitant heart valve.

BACKGROUND OF THE INVENTION

A heart valve may become defective or damaged from degeneration caused by congenital malformation, disease, aging, and the like. When the valve becomes defective or damaged, the leaflets may not function properly to effectively prevent blood flow through the valve when appropriate. For example, when a mitral valve functions properly, the mitral valve prevents regurgitation of blood from the left ventricle into the left atrium when the ventricle contracts. In order to withstand the substantial backpressure and prevent regurgitation of blood into the left atrium during the ventricular contraction, the chordae tendinae hold the anterior and posterior leaflets in place across the opening of the annular ring.

If the annulus of the mitral valve enlarges or dilates to a point where the attached leaflets are unable to fully close the opening (e.g, malcoaptation), regurgitation may occur. Further, valve prolapse, or the forcing of the valve annulus and leaflets into the left atrium by backpressure in the left ventricle, may occur. Adverse clinical symptoms, such as chest pain, cardiac arrhythmias, dyspnea, and the like may manifest in response to regurgitation or valve prolapse. As a result, surgical correction, either by valve repair procedures or by valve replacement, may be required.

Surgical reconstruction or repair procedures may include plication, chordal shortening, or chordal replacement. Another common repair procedure entails remodeling the valve annulus (e.g., annuloplasty) by implantation of a prosthetic ring to help stabilize the annulus and to correct or help prevent valve insufficiency. In situations where the valve leaflets exhibit lesions, reconstruction of one or more valve leaflets by securing grafts or patches to the leaflets, such as over lesions or holes formed in the leaflets, may be necessary. The repair or reconstruction of the leaflets can be complicated and time consuming.

SUMMARY OF THE INVENTION

In one aspect of the present invention, an apparatus is provided for treating regurgitation of blood through a diseased heart valve having at least two leaflets. The apparatus comprises a lollipop-shaped body member having a proximal end portion, a distal end portion, and an intermediate portion extending between the proximal and distal end portions. The intermediate portion includes an expandable occluding member having an adjustable diameter so that, during at least a portion of the cardiac cycle, at least one of the heart leaflets coapts with a portion of the occluding member to mitigate or prevent regurgitation of blood through the diseased heart valve. The proximal end portion is physically connected to the occluding member and includes a connecting mechanism for operably mating with an adjustment member, which is for adjusting the position and diameter of the occluding member within the diseased heart valve. The distal end portion includes an anchoring member for securing the apparatus in a heart chamber containing the diseased heart valve.

In another aspect of the present invention, a method is provided for treating regurgitation of blood through a diseased heart valve having at least two leaflets. One step of the method includes providing a system comprising an apparatus and an adjustment member. The apparatus includes a lollipop-shaped body member having a proximal end portion, a distal end portion, and an intermediate portion extending between the distal end portions. The intermediate portion includes an expandable occluding member having an adjustable diameter. The proximal end portion is physically connected to the occluding member and includes a connecting mechanism operably connected to the adjustment member. The distal end portion includes an anchoring member. The anchoring member is secured in a heart chamber containing the heart valve. The adjustment member is then operated so that at least a portion of the occluding member is securely positioned within the diseased heart valve. The adjustment member is further operated to increase or decrease the diameter of the occluding member so that at least one of the diseased heart valve leaflets coapts with the occluding member during the cardiac cycle.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION

Figure 1:
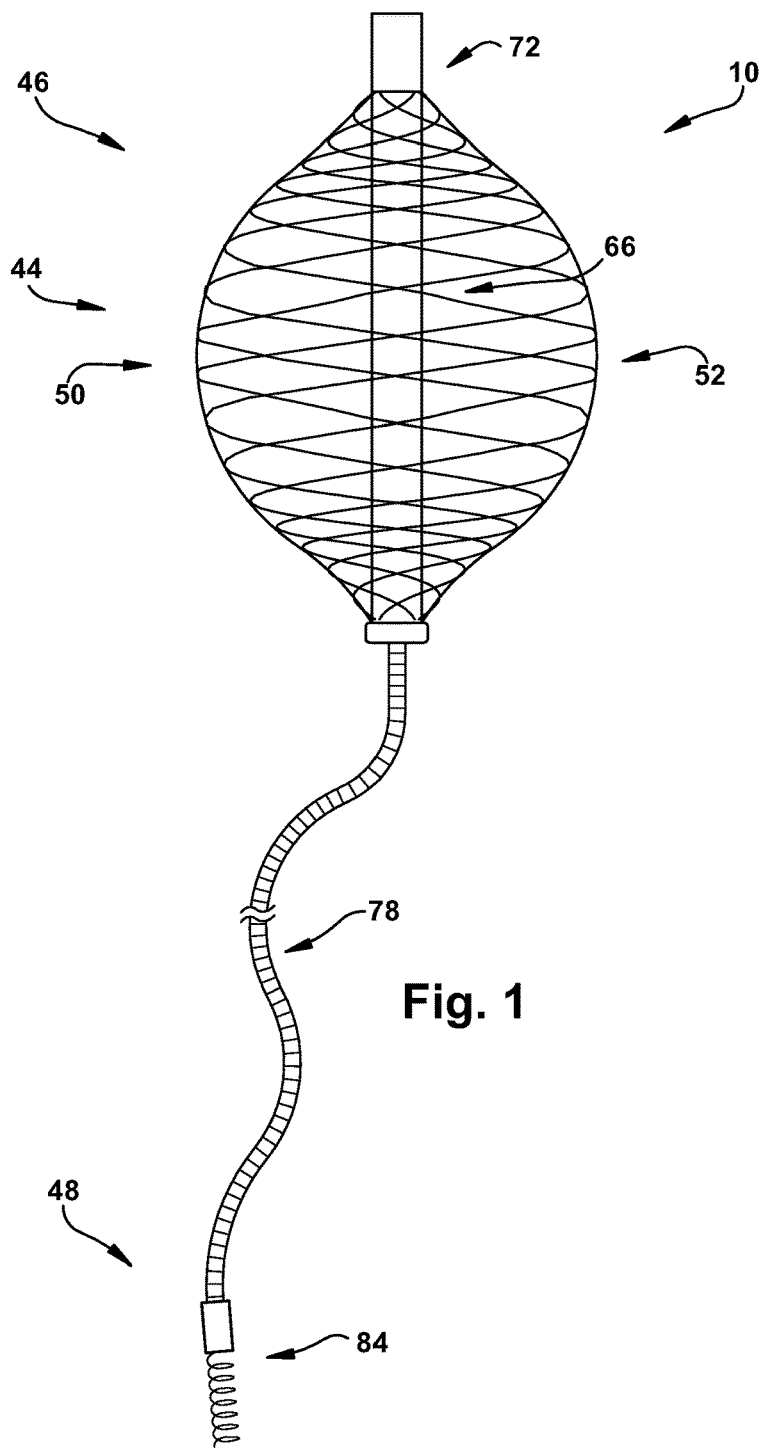
FIG. 1 is a schematic illustration showing an apparatus for treating regurgitation of blood through a diseased heart valve constructed in accordance with one aspect of the present invention.
Figure 6:
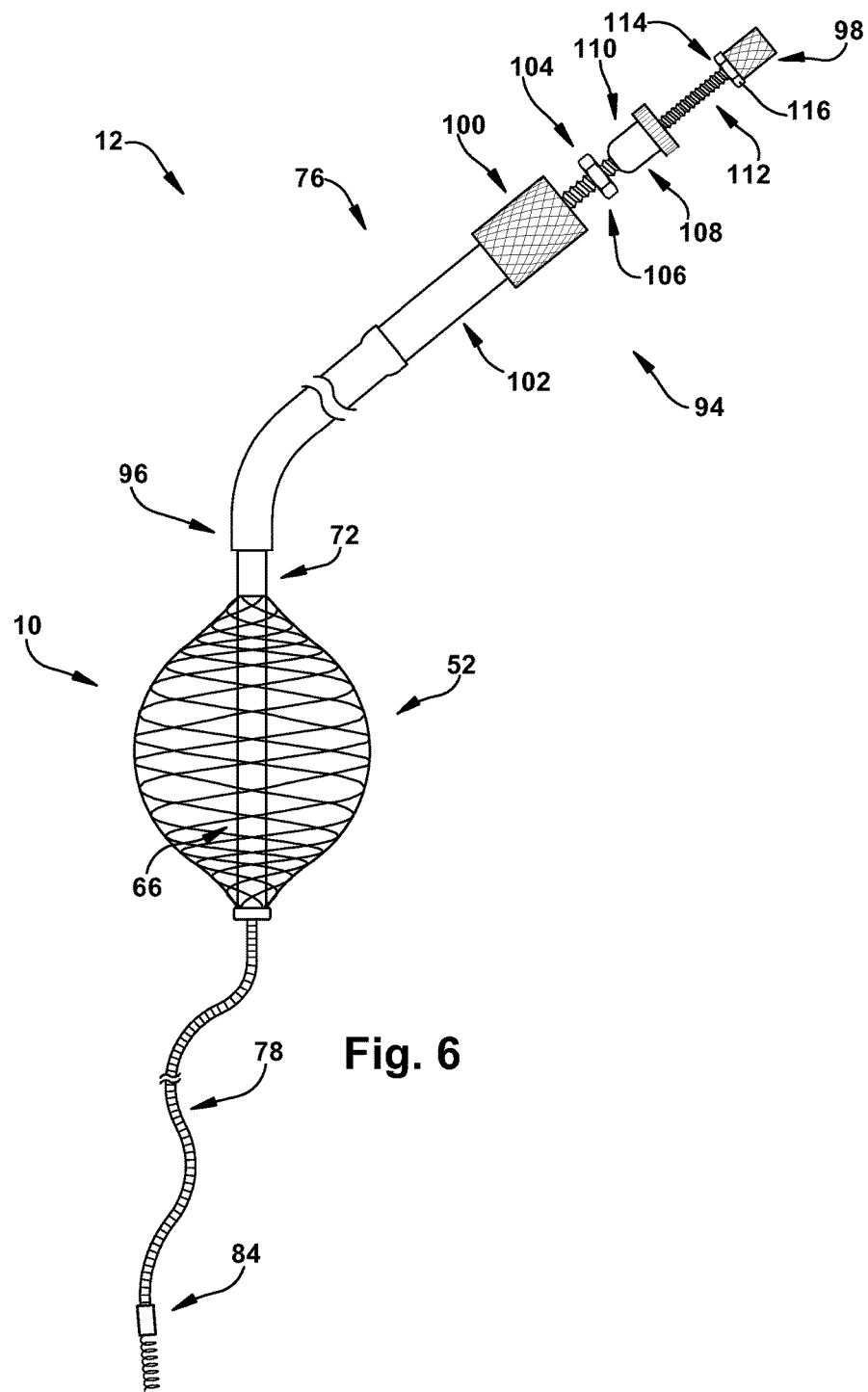
FIG. 6 is a schematic illustration showing a system for treating regurgitation of blood through a diseased heart valve constructed in accordance with another aspect of the present invention.

The present invention relates to an apparatus and method for treating and improving the function of dysfunctional heart valves. More particularly, the present invention relates to a selectively adjustable apparatus that passively assists in closing the native heart valve leaflets to improve valve function of a regurgitant valve. As representative of one aspect of the present invention, FIGS. 1 and 6 illustrate an apparatus 10 and system 12, respectively, for treating regurgitation of blood through a diseased heart valve having at least two leaflets.

Implantable devices for passively assisting with heart valve leaflet coaptation are known in the art. Such devices are typically implanted following imaging studies of the pertinent cardiac structures and/or upon visual inspection (e.g., by a surgeon during an open chest procedure). Either upon implantation or shortly thereafter, however, optimal valve leaflet coaptation may be lost due to unaccounted for variances in device construction and/or heart movement. As described below, the present invention advantageously provides an apparatus 10 (FIG. 1) whose position and dimensions can be selectively adjusted before, during, and after implantation to facilitate optimal valve leaflet coaptation therewith and, thus, ensure that regurgitation of blood through the heart valve is minimized or prevented.

Figure 2:
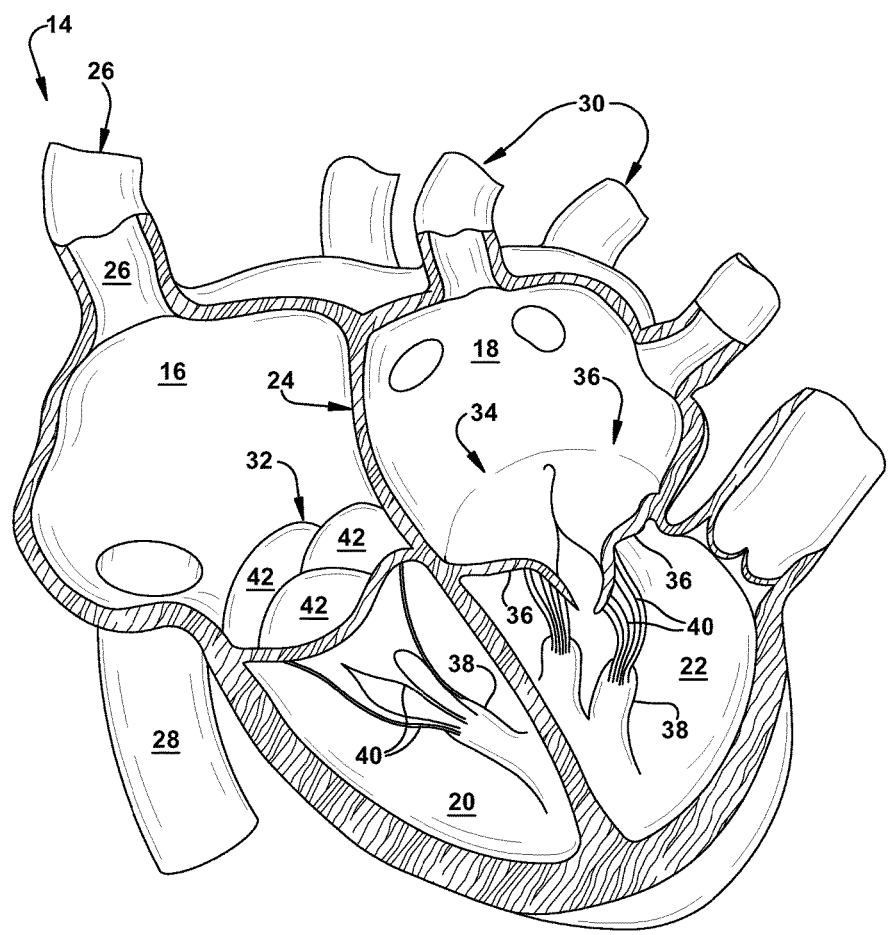
FIG. 2 is a cross-sectional schematic view of a human heart.

FIG. 2 schematically illustrates a human heart 14, which includes the right and left atria 16 and 18 and the right and left ventricles 20 and 22. The right and left atria 16 and 18 are divided by the interatrial septum 24. The thin-walled right atrium 16 receives deoxygenated blood from the superior vena cava 26, the inferior vena cava 28, and from the coronary sinus (not shown). The thin-walled left atrium 18 receives oxygenated blood from pulmonary veins 30. The right and left ventricles 20 and 22 pump oxygenated and deoxygenated blood, respectively, throughout the body, and the pocket-like semilunar pulmonary valve (not shown) and the aortic valve (not shown) prevent reflux into the ventricles. Atrial blood is pumped through the atrioventricular orifices, guarded by the tri-leaflet tricuspid valve 32 on the right side of the heart 14, and the bi-leaflet mitral valve 34 on the left side of the heart. The free edges of the mitral leaflets 36 are attached to the papillary muscles 38 in the right and left ventricles 20 and 22 by chordae tendineae 40. Similarly, the free edges of the tricuspid leaflets 42 are attached to the papillary muscles 38 in the right and left ventricles 20 and 22 by chordae tendineae 40.

One aspect of the present invention includes an apparatus 10 (FIG. 1) for treating regurgitation of blood through a diseased heart valve having at least two leaflets. As shown in FIG. 1, the apparatus 10 comprises a lollipop-shaped body member 44 having a proximal end portion 46, a distal end portion 48, and an intermediate portion 50 extending between the proximal and distal end portions. The intermediate portion 50 includes an expandable occluding member 52 having an outer surface 54 for coapting with at least one heart valve leaflet. As described below, the occluding member 52 assists in closing a diseased heart valve to prevent regurgitation by increasing the coaptation area and/or decreasing the coaptation depth of the valve leaflets. Increasing coaptation of the valve leaflets is generally accomplished by placing the occluding member 52 in a regurgitant valve orifice, thereby providing a surface against which the valve leaflets may abut (i.e., coapt) to close the valve during systole. The occluding member 52 assists in substantially closing the diseased heart valve without altering the shape of the valve annulus and/or repositioning the papillary muscles 38. The presence of the occluding member 52 will block regurgitant blood flow through the diseased heart valve during systole as the leaflets abut against the outer surface 54 of the occluding member 52. In other words, the occluding member 52 "plugs" the regurgitant valve orifice during systole to hinder or prevent blood from leaking through the diseased heart valve.

Figures 3A, 3B:
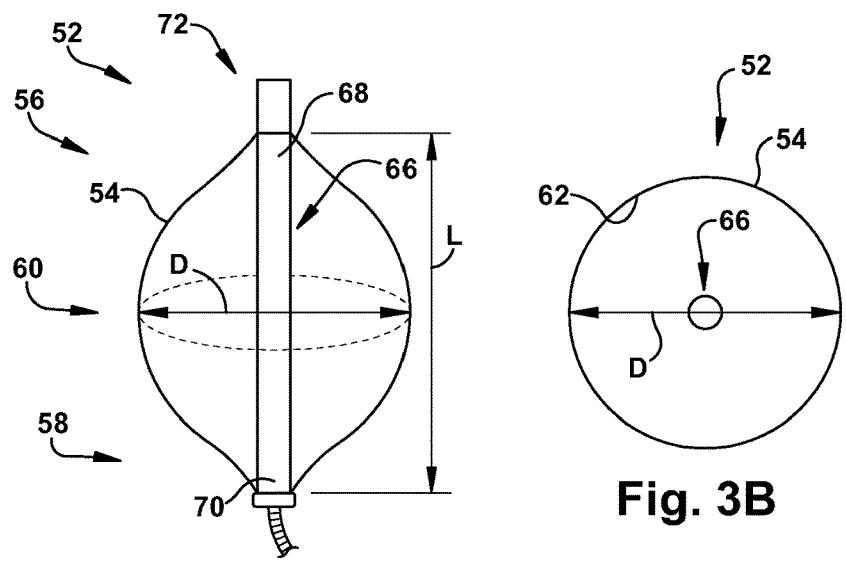
FIG. 3A is a magnified schematic illustration of an occluding member comprising the apparatus in FIG. 1 (cross-hatching omitted for clarity)
FIG. 3B is a top view showing the diameter D of the occluding member in FIG. 3A.
Figures 3C, 3D:
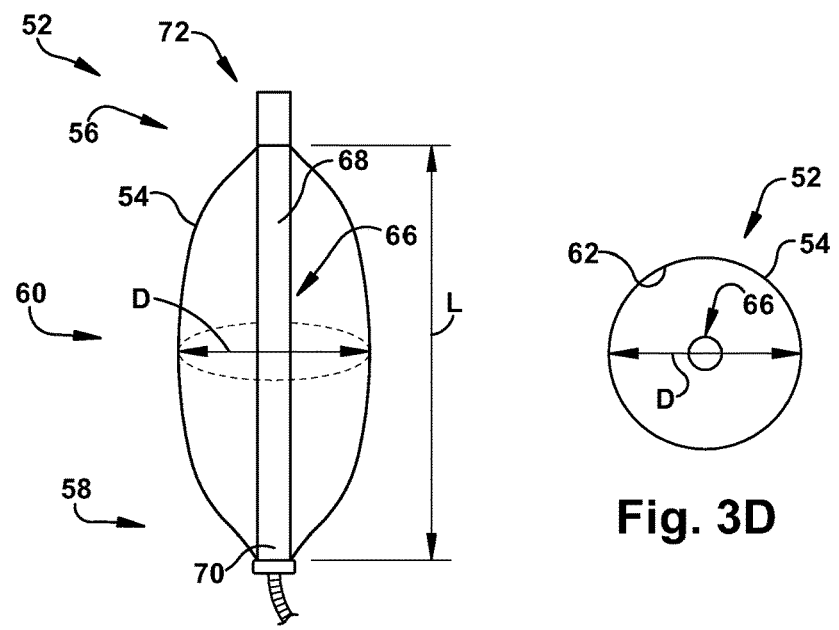
FIG. 3C is a magnified schematic illustration showing an alternative configuration of the occluding member in FIG. 3A (cross-hatching omitted for clarity)
FIG. 3D is a top view showing the diameter D of the occluding member in FIG. 3C.

The occluding member 52 is defined by a first end 56, an opposite second end 58, and a center portion 60 located between the first and second ends. The occluding member 52 is made of any one or combination of materials having a porosity sufficient to allow the flow of blood therethrough. As shown in FIG. 1, for example, the occluding member 52 is made of a flexible mesh-like material, such as stainless steel, titanium alloys, cobalt-chrome alloys, Nitinol, and the like. The occluding member 52 includes a diameter D (FIGS. 3A-B) that extends between oppositely disposed inner surfaces 62 at the center portion 60 of the occluding member. As explained in more detail below, the diameter D can be selectively increased or decreased to vary the configuration of the occluding member 52 from a generally bulbous shape (FIG. 3A) to a generally ovoid shape (FIG. 3C). The ability to selectively increase or decrease the diameter D of the occluding member 52, and thus the surface area available for coaptation, is advantageous because the cross-sectional area of the occluding member can be adjusted in real-time to optimize leaflet coaptation with the outer surface of the occluding member.

Figure 3E:
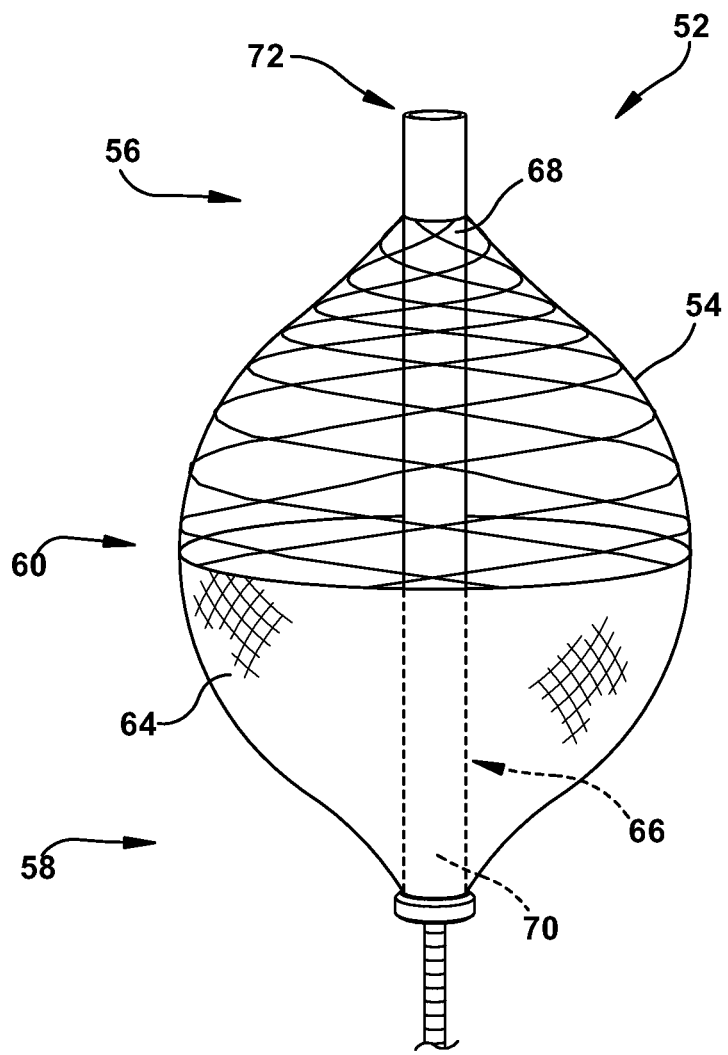
FIG. 3E is a magnified schematic illustration showing an alternative construction of the occluding member in FIG. 1.

As shown in FIG. 3E, the occluding member 52 can additionally or optionally include a biocompatible layer 64. The biocompatible layer 64 can comprise a fine mesh material, such as PTFE, Teflon or ePTFE. The biocompatible layer 64 can extend circumferentially about the occluding member 52 between the center portion 60 and the second end 58 thereof. The biocompatible layer 64 can extend about all or only a portion of the outer surface 54, the inner surface 62, or both. The biocompatible layer 64 can be secured to the occluding member 52 using any known attachment means, such as medical sutures. The biocompatible layer 64 promotes proper leaflet coaptation with the occluding member 52 by preventing undesirable sticking or adherence of the valve leaflets to the occluding member during the cardiac cycle.

The occluding member 52 (FIGS. 3A-D) additionally includes a hollow tube member 66 having first and second ends 68 and 70. The tube member 66 extends axially between the first and second ends 56 and 58 of the occluding member 52. The tube member 66 is defined by a length L that can be selectively increased or decreased. As described in more detail below, the length L of the tube member 66 can be selectively decreased, which increases the diameter D of the occluding member 53 and imparts the occluding member with a generally bulbous shape. The length L of the tube member 66 can alternatively be selectively increased, which decreases the diameter D of the occluding member 52 and imparts the occluding member with an ovoid shape. The tube member 66 can be made of any one or combination of biocompatible and resiliently flexible materials, such as a polymer-based material capable of providing desirable mechanical and fatigue properties.

The first end 56 of the occluding member 52 and the first end 68 of the tube member 66 are secured at the proximal end portion 46 of the apparatus 10 by a connecting mechanism 72 (not shown in detail). The connecting mechanism 72 includes a cylindrical cap or tube 74, as well as an associated mechanism (not shown) for connecting to an adjustment member 76 (FIG. 6). The connecting mechanism 72 (FIGS. 3A-D) is capable of operably interlocking the adjustment member 76 (FIG. 6) with the apparatus 10 and, when desired, disconnecting the adjustment member from the apparatus. Examples of devices or mechanisms capable of operably interlocking the adjustment member 76 and the apparatus 10 include magnetic locks, lock-and-key-styled devices, and the like.

Figures 4A, 4B:
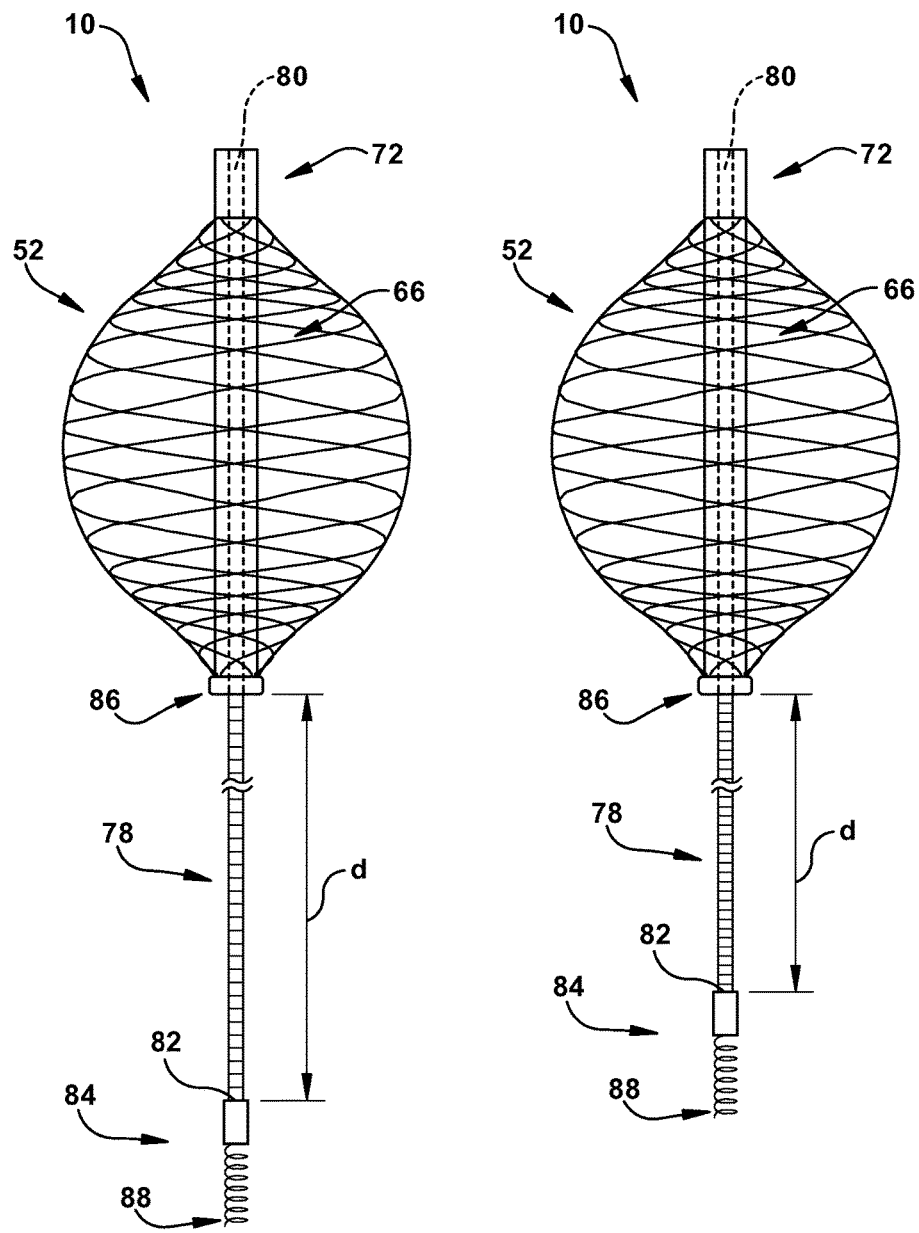
FIGS. 4A-B are schematic illustrations showing different configurations of a wire comprising the apparatus in FIG. 1.

Referring to FIGS. 4A-B, the distal end portion 48 of the apparatus 10 includes a threaded wire 78 having first and second ends 80 and 82. The threaded wire 78 extends through the tube member 66 and includes an anchoring portion 84 for securing the apparatus 10 in a heart chamber containing the diseased heart valve. The threaded wire 78 also extends through a collar 86 having a threaded aperture (not shown). The threaded wire 78 extends a distance d between the collar 86 and the anchoring portion 84. As described in more detail below, the distance d can be selectively increased or decreased to vary the position of the occluding member 52 relative to the diseased heart valve.

The anchoring portion 84 can have any construction or configuration to facilitate secure attachment and implantation of the apparatus 10. As shown in FIGS. 4A-B, the anchoring portion 84 has a spiral or coiled shape and includes a sharpened distal tip 88. The spiral or coiled shape of the anchoring portion 84 facilitates entry and subsequent embedding of the anchoring portion in heart tissue surrounding the diseased heart valve. It will be appreciated that the anchoring portion 84 can have other configurations besides the one shown in FIGS. 4A-B. For example, the anchoring portion 84 can have a clip-like (not shown) or barb-shaped configuration (not shown). As described below, the threaded wire 78 and the compressible tube member 66 collectively form an adjustment mechanism that enables selective adjustment of the position and diameter D of the occluding member 52.

It will be appreciated that the apparatus 10 may include at least one radiographically opaque marking (not shown) to facilitate positioning of the apparatus in a diseased heart valve. The radiographically opaque marking may be located on the occluding member 52 or, alternatively, at any other portion of the apparatus 10. The radiographically opaque marking can be any one or combination of materials or devices with significant opacity. Examples of such radiographically opaque markings include, but are not limited to, a steel mandrel sufficiently thick to be visible on fluoroscopy, a tantalumlpolyurethane tip, a gold-plated tip, bands of platinum, stainless steel or gold, soldered spots of gold, and polymeric materials with a radiographically opaque filter, such as barium sulfate.

Figure 5:
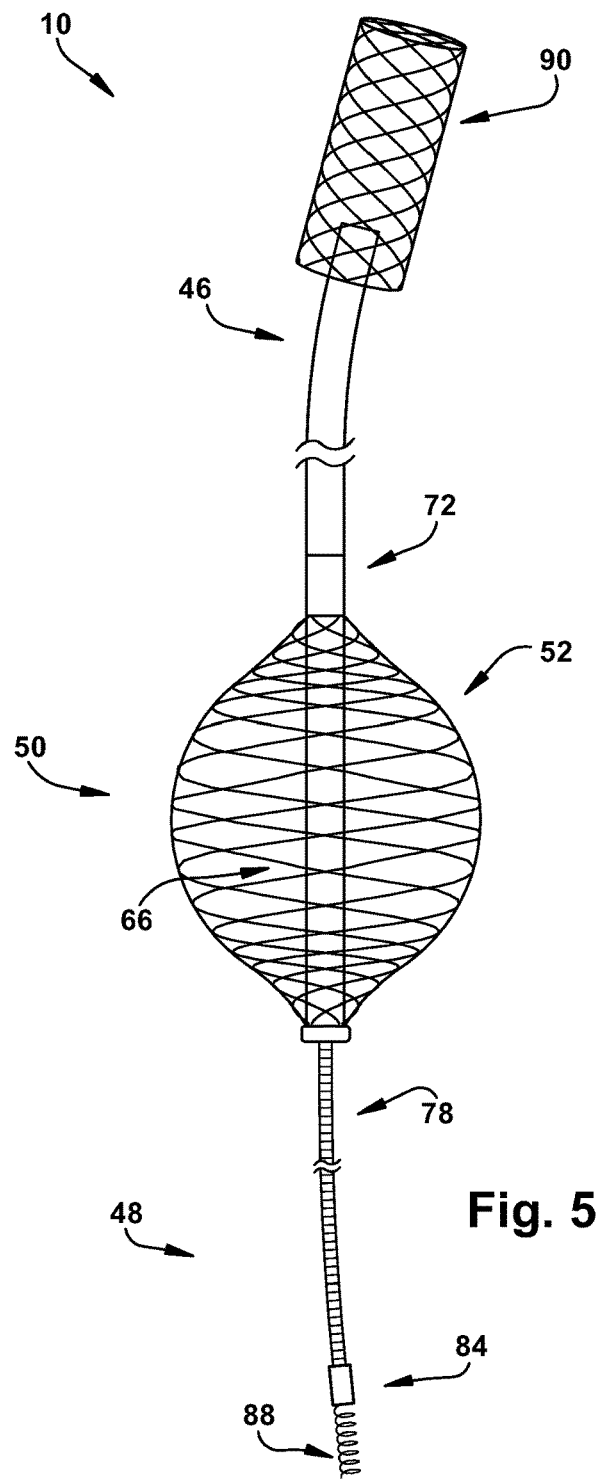
FIG. 5 is a schematic illustration showing an alternative configuration of the apparatus in FIG. 1.

FIG. 5 shows an alternative configuration of the apparatus 10 illustrated in FIG. 1.

As shown in FIG. 5, the apparatus 10 can include at least one expandable support member 90 for anchoring in a blood vessel (e.g., the superior vena cava 26) surrounding a diseased heart valve. The expandable support member 90 can have a stent-like configuration and be physically connected (e.g., directly connected without any intervening components or elements) at the proximal end portion 46 of the apparatus 10. The expandable support member 90 may be a mesh, a zigzag wire, a spiral wire, an expandable stent, or other similar configuration that allows the expandable support member to be collapsed and expanded. The expandable support member 90 can be comprised of a material having a high modulus of elasticity including, for example, cobalt-nickel alloys (e.g., Elgiloy), titanium, nickel-titanium alloys (e.g., Nitinol), cobalt-chromium alloys (e.g., Stellite), nickel-cobalt-chromium-molybdenum alloys (e.g., MP35N), graphite, ceramic, stainless steel, and hardened plastics. The expandable support member 90 may also be made of a radio-opaque material or include radio-opaque markers to facilitate fluoroscopic visualization. Although only one expandable support member 90 is shown in FIG. 5, it will be appreciated that the apparatus 10 can include two or more expandable support members (e.g., connected in series).

Another aspect of the present invention includes a system 12 (FIG. 6) for treating regurgitation of blood through a diseased heart valve having at least two leaflets. The system 12 includes an apparatus 10 and an adjustment member 76. The apparatus 10 is identically constructed as the apparatus described above. As shown in FIG. 6, the adjustment member 76 comprises an elongated body 92 having a proximal control end 94 and an oppositely disposed distal connecting end 96 for mating with the connecting mechanism 72 of the apparatus 10. The proximal control end 94 includes a first handle member 98 for controlling the position of the occluding member 52 relative to the diseased heart valve, and a second handle member 100 for controlling the diameter D of the occluding member.

The body 92 of the adjustment member 76 is comprised of a flexible outer sheath or tubing that terminates in an elongated metal cuff 102, which is operably attached to the second handle member 100. A hollow, threaded screw member 104 extends through the second handle member 100 into the metal cuff 102. A first hexagonal nut 106 for locking the position of the second handle member 100 is disposed about the screw member 104. A first end 108 of the screw member 104 includes a flared portion 110 for receiving a threaded member 112. A first end 114 of the threaded member 112 is physically connected to the first handle member 98. A second hexagonal nut 116 for locking the position of the first handle member 98 is disposed about the threaded member 112. Operation of the system 12, and in particular the adjustment member 76, is described in detail below.

FIGS. 7-11 illustrate another aspect of the present invention including a method for treating regurgitation of blood through a diseased tricuspid valve 118. The method is performed using the system 12 illustrated in FIG. 6. The system 12, for example, can comprise an apparatus 10 and an adjustment member 76 that are similarly or identically constructed as the apparatus and adjustment member described above.

Figure 7:
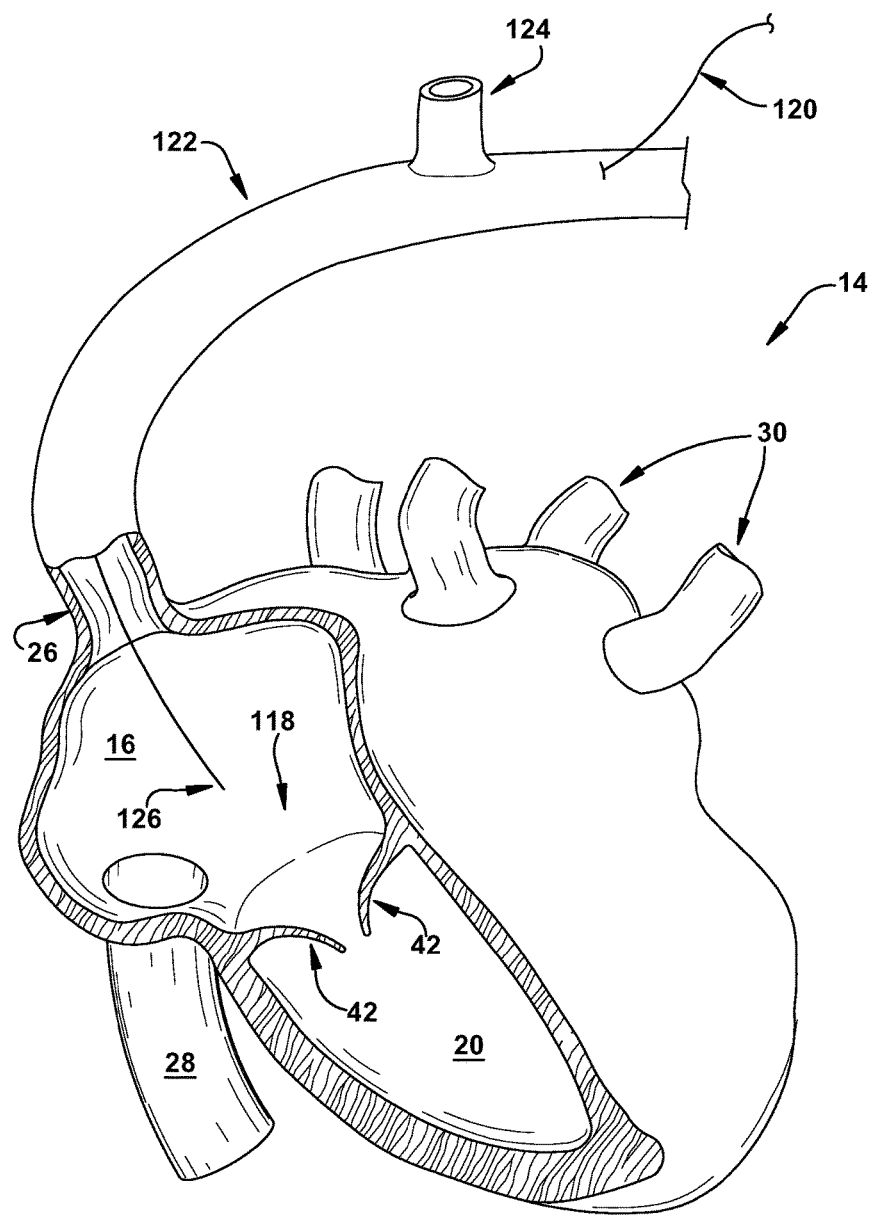
FIG. 7 is a cross-sectional view showing a guidewire extending through a subclavian vein, across the superior vena cava, and into the right atrium.

A percutaneous approach can be used to deliver the apparatus 10 to the diseased tricuspid valve 118. To do so, a guidewire 120 is inserted into a femoral access site, such as a patient's subclavian vein 122 (FIG. 7), jugular vein 1254 or femoral vein (not shown). Where the guidewire 120 is inserted into a subclavian vein 122, image guidance (e.g., fluoroscopy, ultrasound, magnetic resonance, computed tomography, or combinations thereof) can be used to steer through the guidewire through the subclavian vein, across the superior vena cava 26, and into the right atrium 16 (as shown in FIG. 7).

Once a distal end 126 of the guidewire 120 has reached the right atrium 16, the distal end may be hinged downward toward the diseased tricuspid valve 118. The guidewire 120 may then be urged through the diseased tricuspid valve 118 so that the distal end 126 enters the right ventricle 20. The guidewire 120 may next be positioned in the right ventricle 20 so that the guidewire is securely positioned within the superior vena cava 26, the right atrium 16, and the subclavian vein 122.

After the guidewire 120 is secured in the patient's heart 14, a catheter 128 (FIG. 8) may be passed over the guidewire and advanced into the right atrium 16. If it has not been done so already, the apparatus 10 is mated with the adjustment member 76 and then attached to a proximal end (not shown) of the guidewire 120. Next, an axial force is then applied to the proximal control end 94 of the adjustment member 76 so that the apparatus 10 is passed over the guidewire 120. The apparatus 10 is advanced along the guidewire 120 until the apparatus reaches a distal end portion 130 of the catheter 128.

Figure 8:
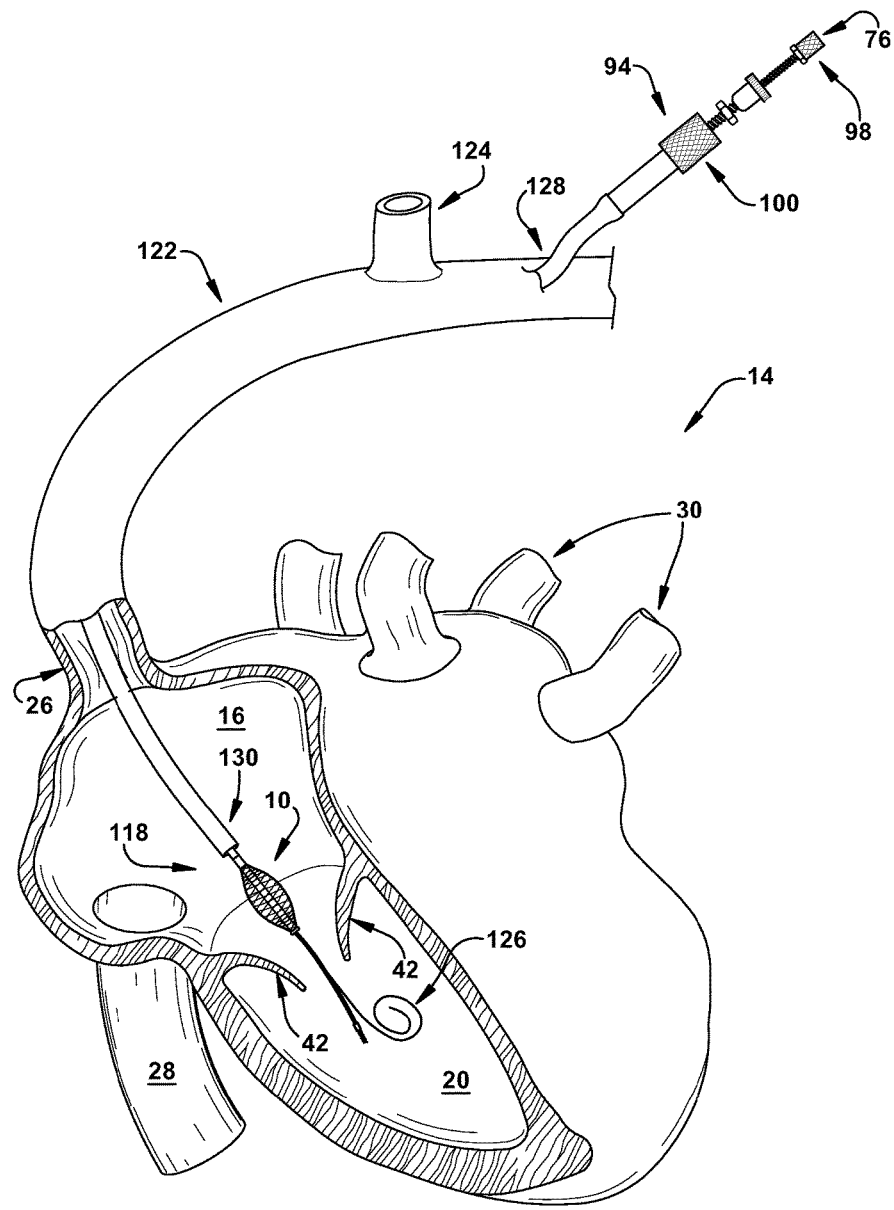
FIG. 8 is a cross-sectional view showing the apparatus of FIG. 1 partly deployed in a diseased tricuspid valve.

Upon reaching the distal end portion 130 of the catheter 128, the apparatus 10 is progressively freed from the catheter as shown in FIG. 8. As the apparatus 10 is progressively freed from the catheter 128, the position of the apparatus within the heart 14 can be monitored, controlled, and/or quality assured by imaging systems of various kinds. For example, X-ray machines, fluoroscopic machines, ultrasound, CT, MRI, PET, and other imaging devices may be used.

Once the apparatus 10 is freed from the catheter 128, the apparatus may be appropriately positioned in the heart 14. More particularly, the anchoring portion 84 may be urged toward the wall of the right ventricle 20 until the sharpened tip 88 contacts the right ventricular wall (FIG. 9), and the anchoring portion is positioned so that the occluding member 52 is at or slightly below the level of the tricuspid annulus. It will be appreciated that depending upon the location and geometry of the regurgitant tricuspid valve orifice, the occluding member 52 may be suspended at any one of a number of different positions. For example, the occluding member 52 may be positioned approximately level to the tricuspid annulus. Alternatively, the occluding member 52 may be positioned so that at least a portion of the occluding member is positioned below the free ends of the tricuspid valve leaflets 42.

Figure 9:
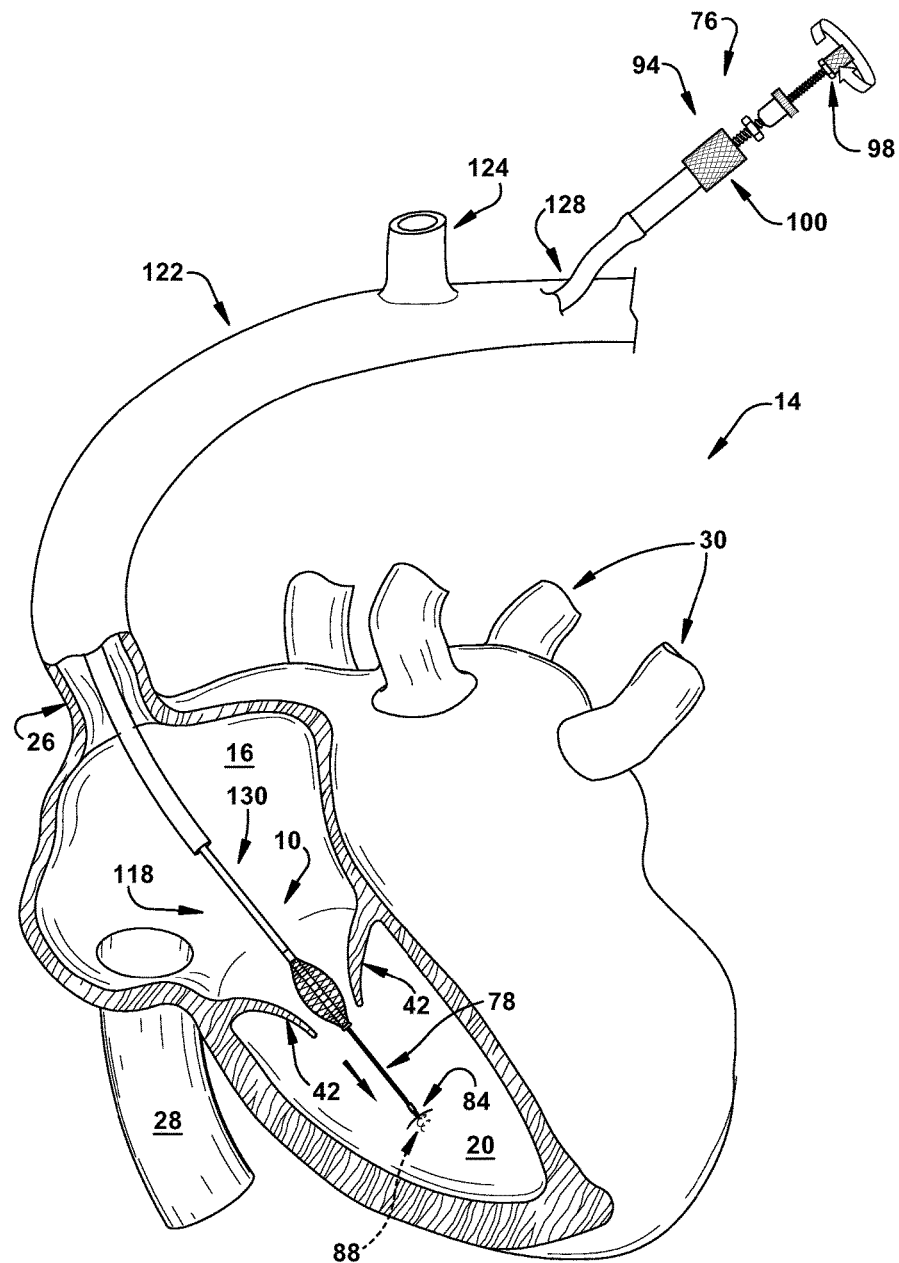
FIG. 9 is a cross-sectional view showing the apparatus in FIG. 8 being anchored in the right ventricle.
Figure 10:
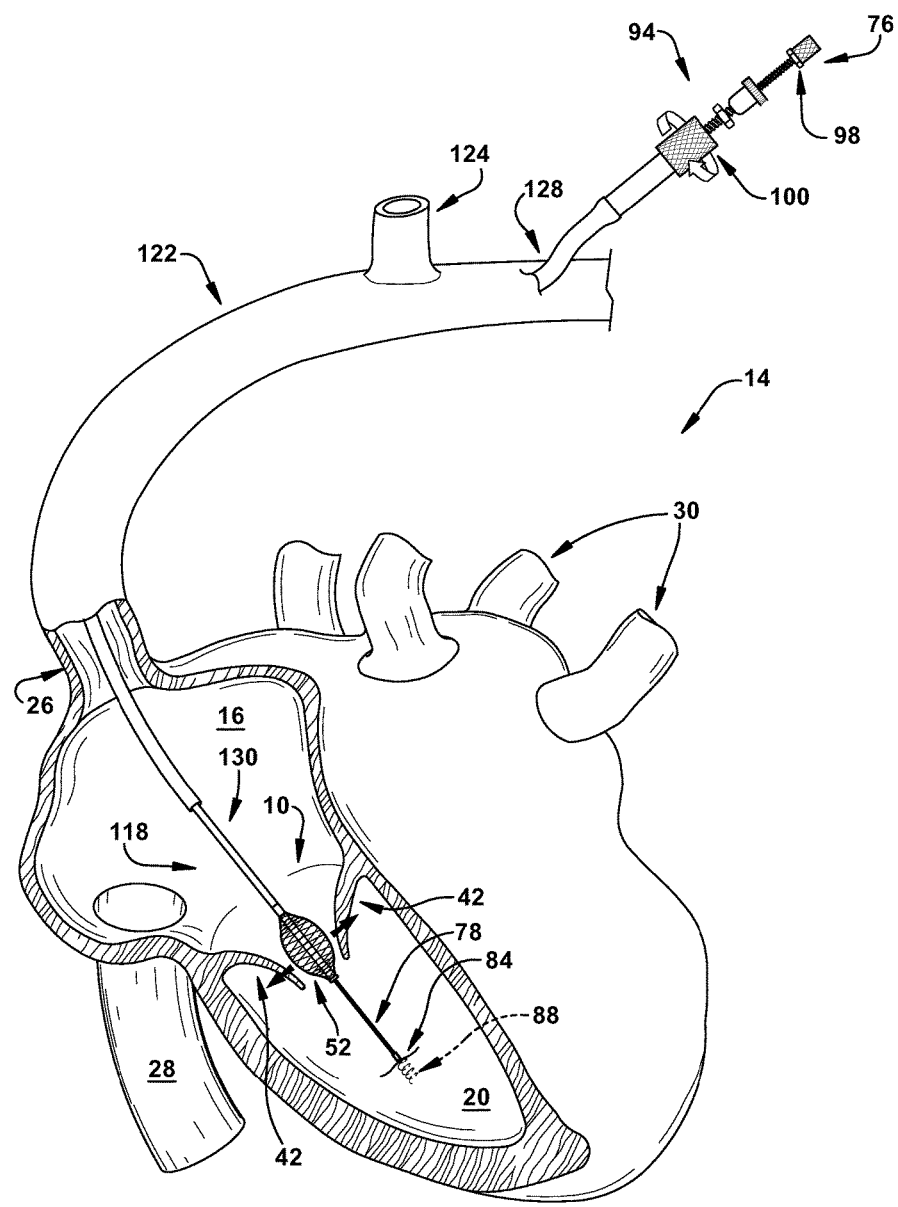
FIG. 10 is a cross-sectional view showing the diameter D of the occluding member in FIG. 9 being increased.
Figure 11:
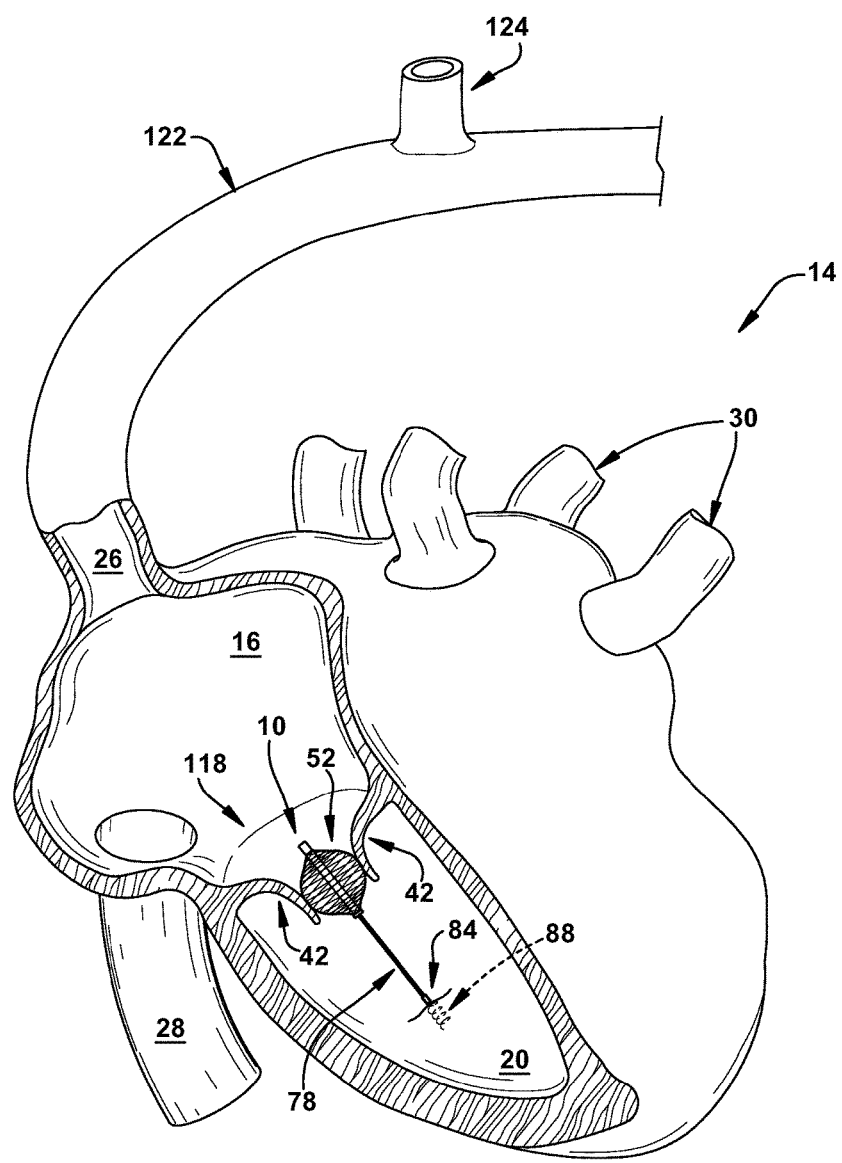
FIG. 11 is a cross-sectional view showing the apparatus in FIG. 10 deployed in the diseased tricuspid valve.

The first handle member 98 of the adjustment member 72 is then turned in clockwise manner, which causes the threaded wire 78 to be extruded from the collar 86 and force the sharpened tip 88 of the anchoring portion 84 into the heart tissue (as indicated by the arrow in FIG. 9). The first handle member 98 is operated (i.e., turned in clockwise manner) until the anchoring portion 84 is substantially or entirely embedded within the right ventricular wall. If needed, the position of the occluding member 52 relative to the diseased tricuspid valve 118 can be adjusted. To move the occluding member 52 in a superior direction, for example, the first handle member 98 can be rotated in a counter-clockwise direction, which increases the distance d of the threaded wire 78. Conversely, the occluding member 52 can be moved in an inferior direction by rotating the first handle member 98 in a clockwise direction, which decreases the distance d of the threaded wire 78.

After the occluding member 52 is optimally positioned in or about the diseased tricuspid valve 118, the diameter D of the occluding member can be adjusted to ensure proper coaptation of the tricuspid leaflets 42 with the outer surface 54 of the occluding member. To increase the diameter D of the occluding member 52 (indicated by arrows in FIG. 10), for example, the second handle member 100 is rotated in a clockwise manner. Alternatively, the second handle member 100 can be rotated in a counter-clockwise manner to decrease the diameter D of the occluding member 52. Coaptation of the tricuspid valve leaflets 42 with the outer surface 54 of the occluding member 52 may be monitored by any image-based means. Where the occluding member 52 has opacity, for example, MRI or CT may be used to monitor the degree of coaptation between the tricuspid leaflets 42 and the occluding member 52. Any further adjustments to the diameter D of the occluding member 52 can then be made to ensure optimal coaptation of the tricuspid leaflets 42.

Once the apparatus 10 is appropriately positioned in the heart 14 of the patient (FIG. 11), the adjustment member 76 can be disconnected from the proximal end portion 46 of the apparatus and, along with the guidewire 120 (if it has not been done so already), withdrawn from the patient's vasculature. With the occluding member 52 appropriately positioned in the regurgitant tricuspid valve orifice, at least one leaflet 42 of the tricuspid valve 118 can coapt with the outer surface 54 of the occluding member. Consequently, the valve leaflets 42 abut the occluding member 52 and buttress the tricuspid valve 118 so that the regurgitant blood flow through the diseased tricuspid valve is substantially reduced or eliminated during systole.

Figure 16:
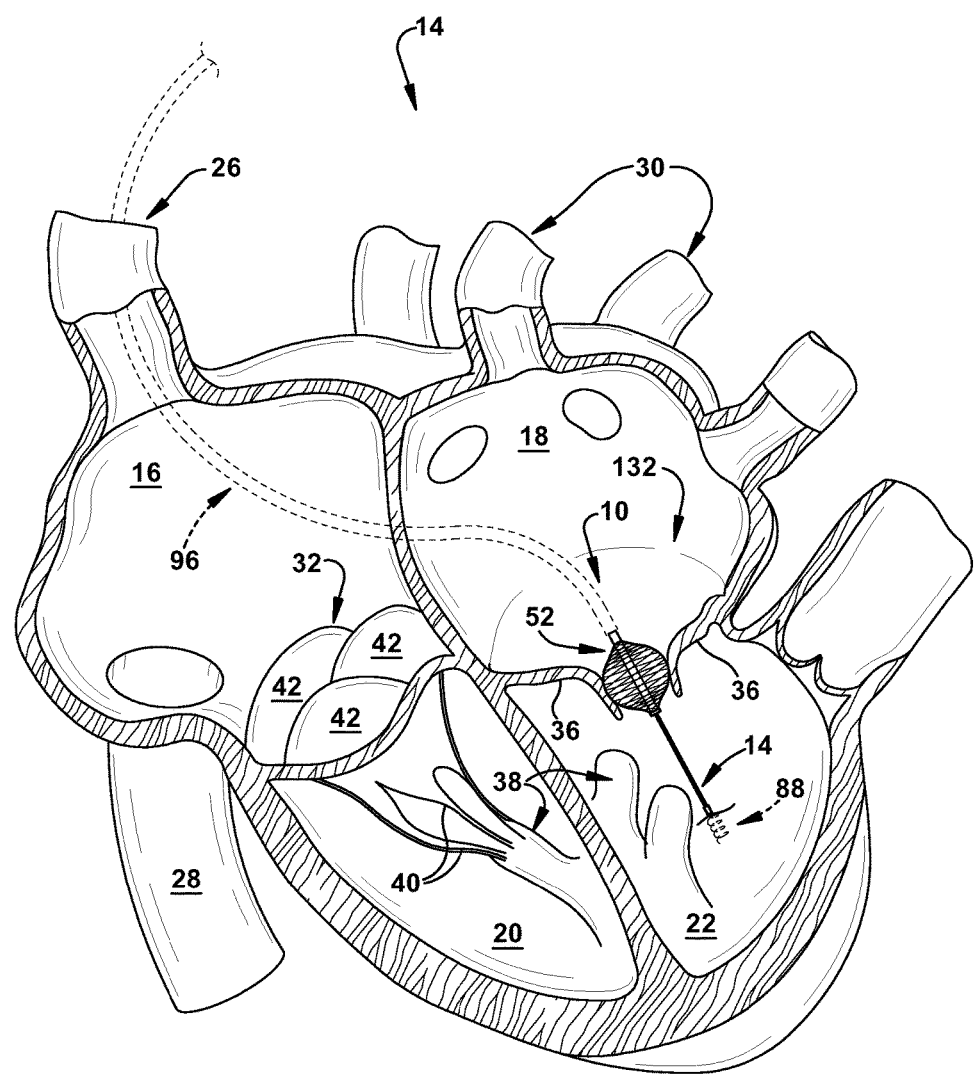
FIG. 16 is a cross-sectional view showing the apparatus in FIG. 15 deployed in the diseased mitral valve.

It will be appreciated that the adjustment member 76 may not be detached from the apparatus 10 following implantation of the apparatus 10. Instead, the adjustment member 76 can be secured within the patient in a pacemaker-like manner following implantation of the apparatus 10 (indicated by reference number 96 in FIG. 16). Using a transvenous approach through a subclavian vein 122, for example, the proximal control end 94 of the adjustment member 76 may be sutured to muscle tissue beneath the outer skin of the patient to maintain the position of the proximal control end. A protective sheath (not shown) may be provided around the proximal control end 94. It is possible to access the proximal control end 94 of the adjustment member 76 at a later time if, for example, it is required to alter the position and/or diameter of the occluding member 52, or to remove the apparatus 10, for example, if the apparatus becomes infected. Access may be gained by removing the protective sheath and exposing the proximal control end 94 or any other portion of the body 92 that is connectable to the proximal control end.

It will also be appreciated that a balloon-based approach may be used to first size the diseased tricuspid valve 118 prior to implantation of the apparatus 10. Such an approach is described in U.S. Pat. No. 7,901,454 to Kapadia et al., the entirety of which is hereby incorporated by reference.

FIGS. 12-16 illustrate another aspect of the present invention including a method for treating regurgitation of blood through a diseased mitral valve 132. The method is performed using the system 12 illustrated in FIG. 2. The system 12, for example, can comprise an apparatus 10 and an adjustment member 76 that are similarly or identically constructed as the apparatus and adjustment member described above.

Figure 12:
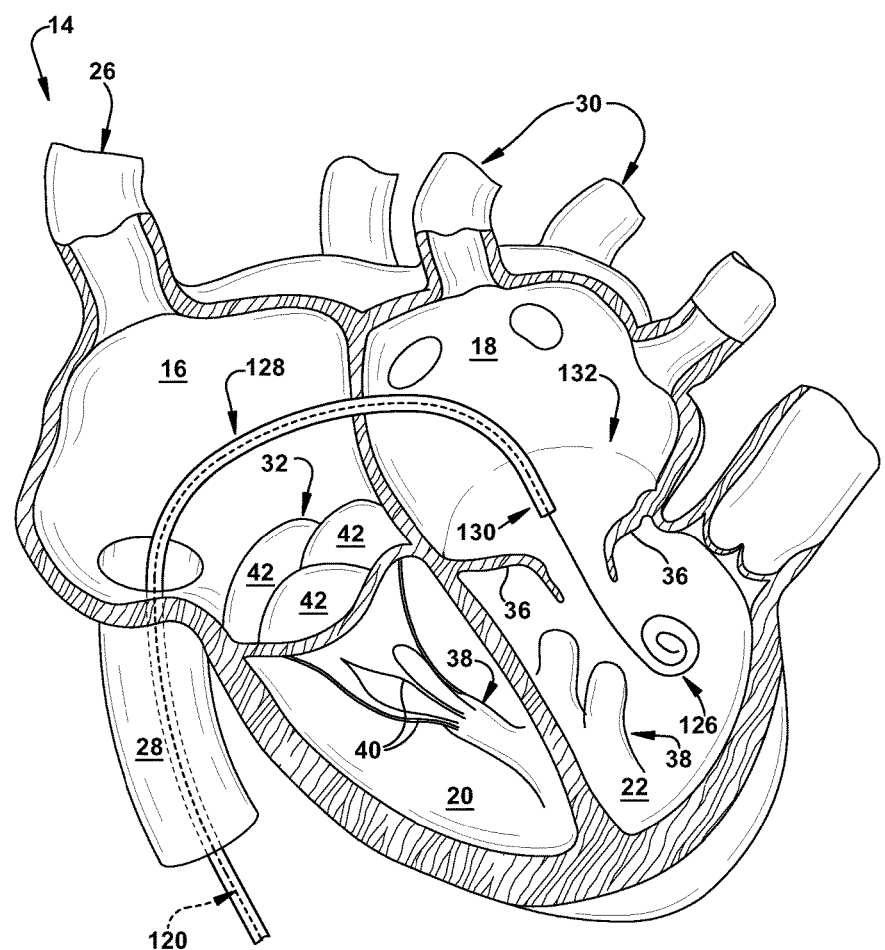
FIG. 12 is a cross-sectional view showing a catheter advanced over a guidewire into the left ventricle.

To treat regurgitation of blood through the diseased mitral valve 132, a guidewire 120 is first inserted into a patient's body via a femoral vein (not shown), jugular vein 124, another portion of the patient's vasculature, or directly into the body through a chest incision. Under image guidance (e.g., fluoroscopy, ultrasound, magnetic resonance, computed tomography, or combinations thereof), the guidewire 120 may be steered through the patient's vasculature into the inferior vena cava 28, for example. The guidewire 120 is then passed across the right atrium 16 so that a distal end 126 of the guidewire pierces the interatrial septum 24 (FIG. 12). The guidewire 120 is extended across the left atrium 18 and then downward through the diseased mitral valve 132 so that the distal end 126 of the guidewire is securely positioned in the left ventricle 22.

After the guidewire 120 is appropriately positioned in the patient's heart 14, a catheter 128 is passed over the guidewire. The catheter 128 is then passed over the guidewire 120 and advanced into the left atrium 18. If it has not been done so already, the apparatus 10 is mated with the adjustment member 76 and attached to a proximal end (not shown) of the guidewire 120. An axial force is then applied to the proximal control end 94 of the adjustment member 76 so that the apparatus 10 is passed over the guidewire 120. The apparatus 10 is advanced along the guidewire 120 until the apparatus reaches a distal end portion 130 of the catheter 128.

Figure 13:
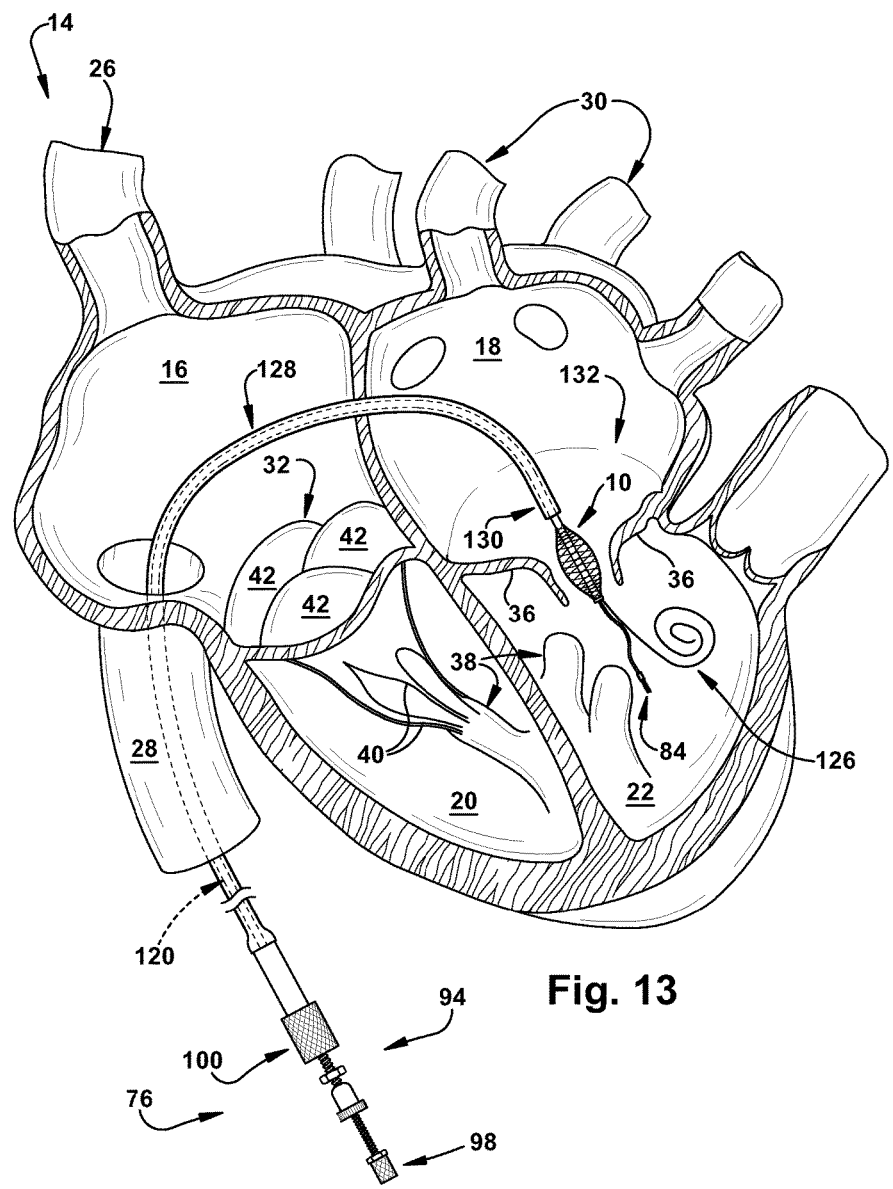
FIG. 13 is a cross-sectional view showing the apparatus of FIG. 12 partly deployed in a diseased mitral valve.

Upon reaching the distal end portion 130 of the catheter 128, the apparatus 10 is progressively freed from the catheter as shown in FIG. 13. As the apparatus 10 is progressively freed from the catheter 128, the position of the apparatus within the heart 14 can be monitored, controlled, and/or quality assured by imaging systems of various kinds. For example, X-ray machines, fluoroscopic machines, ultrasound, CT, MRI, PET, and other imaging devices may be used.

Figure 14:
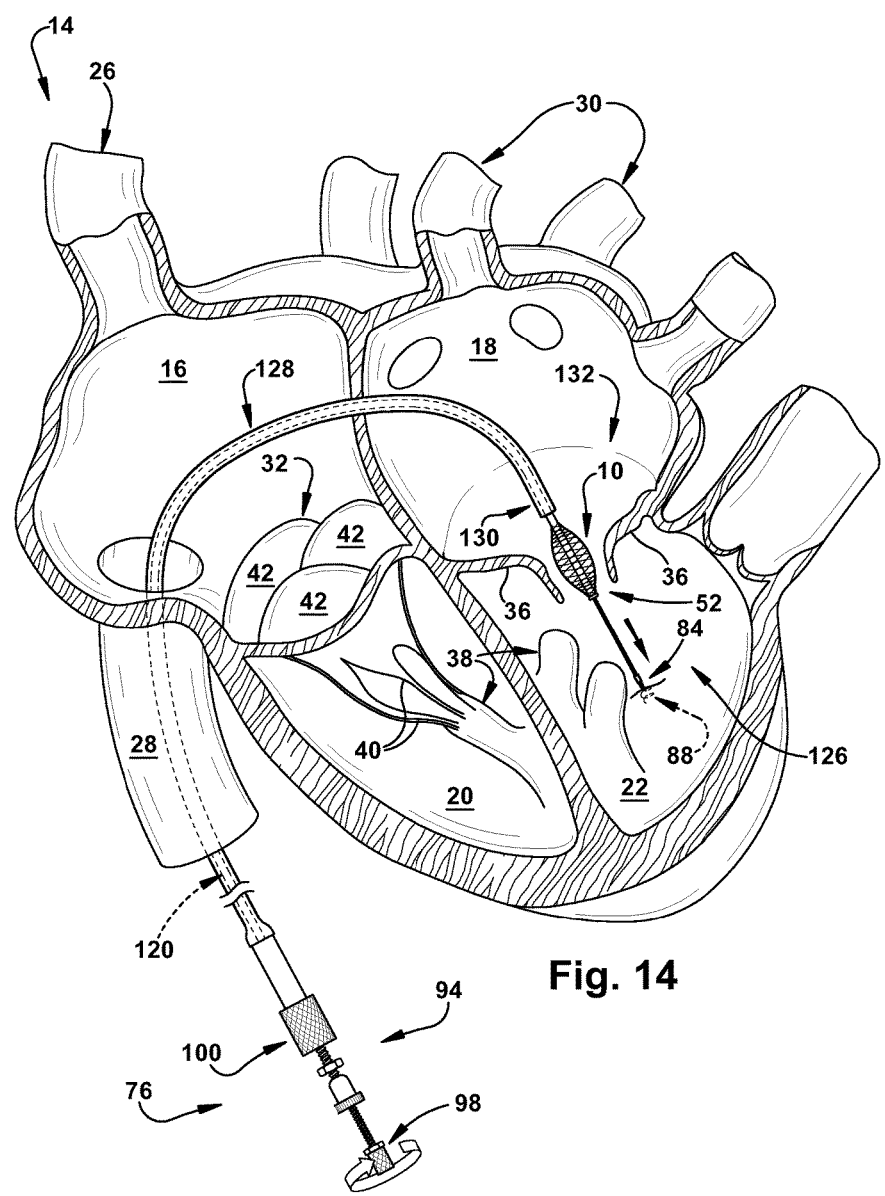
FIG. 14 is a cross-sectional view showing the apparatus in FIG. 13 being anchored in the left ventricle.
Figure 15:
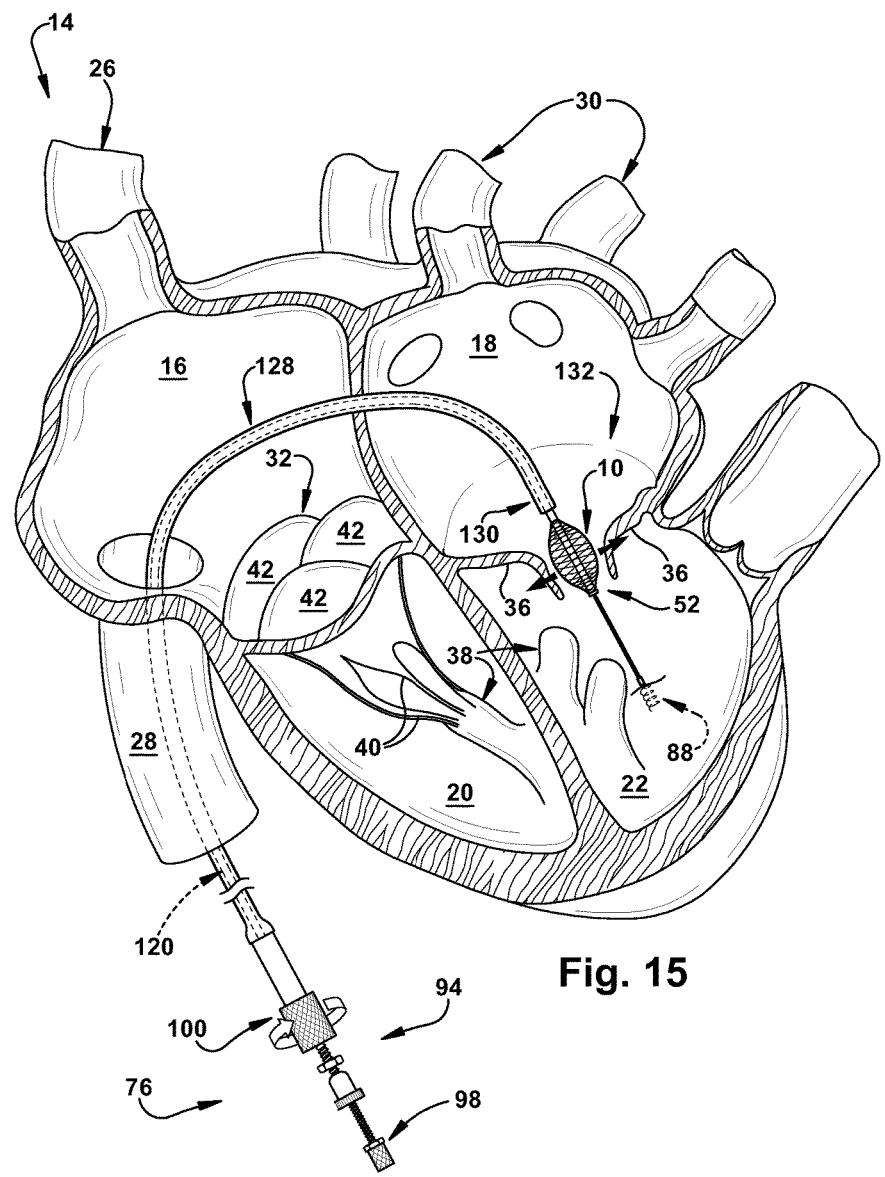
FIG. 15 is a cross-sectional view showing the diameter D of the occluding member in FIG. 14 being increased.

Once the apparatus 10 is freed from the catheter 128, the apparatus may be appropriately positioned in the heart 14. More particularly, the anchoring portion 84 may be urged toward the wall of the left ventricle 22 until the sharpened tip 88 contacts the left ventricular tissue (FIG. 14). The anchoring portion 84 is positioned within the heart 14 so that the occluding member 52 is positioned at or slightly below the level of the mitral annulus. Depending upon the location and geometry of the regurgitant mitral valve orifice, the occluding member 52 may be suspended at any one of a number of different positions. For example, the occluding member 52 may be positioned approximately level to the mitral annulus. Alternatively, the occluding member 52 may be positioned so that at least a portion of the occluding member is positioned below the free ends of the mitral valve leaflets 36.

The first handle member 98 of the adjustment member 76 can then be turned in clockwise manner, which causes the threaded wire 78 to be extruded from the collar 86 and force the sharpened tip 88 of the anchoring portion 84 into the heart tissue (indicated by arrow in FIG. 14). The first handle member 98 is operated (i.e., turned in clockwise manner) until the anchoring portion 84 is substantially or entirely embedded within the heart tissue of the left ventricle 22. If needed, the position of the occluding member 52 relative to the diseased mitral valve 132 can be adjusted. To move the occluding member 52 in a superior direction, for example, the first handle member 98 can be rotated in a counter-clockwise direction, which increases the distance d of the threaded wire 78. Conversely, the occluding member 52 can be moved in an inferior direction by rotating the first handle member 98 in a clockwise direction and thereby decreasing the distance d of the threaded wire 78.

After the occluding member 52 is optimally positioned relative to the diseased mitral valve 132, the diameter D of the occluding member can be adjusted to ensure proper coaptation of the mitral leaflets 36 with the outer surface 54 of the occluding member. To increase the diameter D of the occluding member 52 (indicated by arrows in FIG. 15), for example, the second handle member 100 is rotated in a clockwise manner. Alternatively, the second handle member 100 can be rotated in a counter-clockwise manner to decrease the diameter D of the occluding member 52. Coaptation of the mitral valve leaflets 36 with the outer surface 54 of the occluding member 52 may be monitored by any image-based means. Where the occluding member 52 has opacity, for example, MRI or CT may be used to monitor the degree of coaptation between the mitral leaflets 36 and the occluding member. Any further adjustments to the diameter D of the occluding member 52 can then be made to ensure optimal leaflet coaptation.

After the apparatus 10 is appropriately positioned in the heart 14 of the patient (FIG. 16), the adjustment member 76 is disconnected from the proximal end portion 46 of the apparatus and, along with the guidewire 120 (if it has not been done so already), withdrawn from the patient's vasculature. With the occluding member 52 appropriately positioned in the regurgitant mitral valve orifice, at least one leaflet 36 of the mitral valve 132 can coapt with the outer surface 54 of the occluding member. Consequently, the mitral valve leaflets 36 abut the occluding member 52 and buttress the mitral valve 132 so that the regurgitant blood flow through the diseased mitral valve is substantially reduced or eliminated during systole.

It will be appreciated that the adjustment member 76 may not be detached from the apparatus 10 following implantation of the apparatus and, rather, that the adjustment member can be secured within the patient in a pacemaker-like manner (as described above). For example, the adjustment member 76 can be included as part of a pacemaker-like container (not shown) that allows remote adjustment of the apparatus 10 (e.g., via a wand, such as a magnetic wand) without opening the pocket housing the adjustment member and/or container. It will also be appreciated that a balloon-based approach may be used to first size the mitral valve 132 prior to implantation of the apparatus 10 as described in U.S. Pat. No. 7,901,454.

From the above description of the invention, those skilled in the art will perceive improvements, changes and modifications. For example, the apparatus 10 may be delivered to the heart 14 via a non-percutaneous method, such as an open chest procedure. Such improvements, changes, and modifications are within the skill of the art and are intended to be covered by the appended claims.

Having described the invention, I claim:

1. A method for treating regurgitation of blood through a diseased heart valve having at least two leaflets, said method comprising the steps of:

providing a system comprising an apparatus and an adjustment member, the apparatus including a lollipop-shaped body member having a proximal end portion, a distal end portion, and an intermediate portion extending between the distal end portions, the intermediate portion including an expandable occluding member having an adjustable diameter, the proximal end portion being physically connected to the occluding member and including a connecting mechanism that is operably connected to the adjustment member, and the distal end portion including an anchoring member;

securing the anchoring member in a heart chamber containing the heart valve;

operating the adjustment member so that the anchoring member is securely positioned within heart tissue associated with the diseased heart valve; and operating the adjustment member to increase or decrease the diameter of the occluding member so that at least one of the diseased heart valve leaflets coapts with the occluding member during the cardiac cycle;

wherein after the anchoring member is secured in the heart chamber, blood is permitted to flow through at least a portion of the occluding member.

2. The method of claim 1, wherein said step of securing the anchoring member in a heart chamber further comprises the step of introducing the apparatus and a portion of the adjustment member into the vasculature of a subject.

3. The method of claim 1, wherein the diseased heart valve is a mitral valve.

4. The method of claim 1, wherein the diseased heart valve is a tricuspid valve.

5. The method of claim 1, wherein said step of operating the adjustment member so that the anchoring member is securely positioned within heart tissue associated with the diseased heart valve further includes the step of turning a first handle portion in a clockwise manner so that the anchoring member is embedded within heart tissue surrounding the heart valve.

6. The method of claim 1, wherein said step of operating the adjustment member to increase or decrease the diameter of the occluding member further includes the step of turning a second handle portion in a clockwise or counterclockwise manner, respectively.

7. The method of claim 1, further comprising the step of securing the adjustment member within the subject by providing a protective sheath around the proximal control end of the adjustment member to form a pocket, and suturing the proximal control end to muscle beneath the outer surface of the subject.

8. The method of claim 7, wherein the adjustment member is adjusted without opening the pocket.

* * * * *